US00PP22127P2

(12) United States Plant Patent
Deuter

(10) Patent No.: US PP22,127 P2
(45) Date of Patent: Sep. 6, 2011

(54) ***MISCANTHUS* PLANT NAMED 'MBS 1002'**

(50) Latin Name: ***Miscanthus* sp.**
Varietal Denomination: MBS 1002

(75) Inventor: Martin Deuter, Wanzleben (DE)

(73) Assignee: Mendel Biotechnology, Inc., Hayward, CA (US)

( * ) Notice: Subject to any disclaimer, the term of this patent is extended or adjusted under 35 U.S.C. 154(b) by 0 days.

(21) Appl. No.: 12/584,496

(22) Filed: Sep. 4, 2009

Related U.S. Application Data

(63) Continuation-in-part of application No. 12/387,444, filed on May 1, 2009, which is a continuation-in-part of application No. 12/387,429, filed on May 1, 2009, which is a continuation-in-part of application No. 12/387,437, filed on May 1, 2009, now abandoned.

(60) Provisional application No. 61/050,162, filed on May 2, 2008.

(51) Int. Cl.
*A01H 5/00* (2006.01)

(52) U.S. Cl. ..... Plt./384

(58) Field of Classification Search ..... Plt./384
See application file for complete search history.

(56) References Cited

OTHER PUBLICATIONS

"'Nagara' eine neue *Miscanthus*-Sorte für die Biomassegewinnung" ("Nagara, a new *Miscanthus* varierty for biomass production"), (Apr. 9, 2008), Tinplant Biotechnik und Pflanzenvermehrung GmbH, website. Leaflet created in and distributed from Aug. 2007.

Allen, D. (Jan. 10, 2008). "Genetic Improvement at Mendel Biotechnology," 5th Annual SRI Symposium, *Miscanthus* at the University of Illinois.

Gutterson, N. (Aug. 19, 2008) "Bottlenecks in Feedstock Production: Can Biotechnology Address These?," at the International Conference for on Sorghum for Biofuels, Aug. 19-22, 2008, Houston Texas.

Gutterson, N. (Jan. 17, 2008). "Plant Biotechnology and Cellulosic Ethanlo Production," Second Decade of Crop Biotechnology Farm Foundation Conference, Jan. 17-18, 2008, Washington, D.C.

Ivanic, R. (May 19, 2009) "*Miscanthus* Potential for Second Generation Biofuels," 2nd Generation Biofuels Symposium, West Lafayette, IN.

Münnich, C. and Jakob, K. (Nov. 27, 2008). "*Miscanthus* —Breeding at Tinplant for US market," International *Miscanthus* Meeting, Nov. 27-28, 2008, Switzerland.

Pude, R. *Miscanthus* International Meeting in Trier, Germany (Nov. 7-8, 2006) www.miscanthus.de/texte/Pressebericht2006.htm. Nagara and Amuri varieties introduced, order forms distributed.

Zhang, J. (Apr. 26-27, 2007). "Lignocellulosic Feedstock Improvement", Fueling Change With Renewable Energy symposium, University of Illinois at Urbana-Champaign.

*Primary Examiner* — Susan McCormick Ewoldt
(74) *Attorney, Agent, or Firm* — Cooley LLP

(57) ABSTRACT

A new and distinct cultivar of *Miscanthus* named 'MBS 1002', generally characterized by its rigorous growth rate, high biomass yield and high tiller density.

11 Drawing Sheets

CROSS-REFERENCE TO RELATED APPLICATIONS

This application is a continuation-in-part of U.S. patent application Ser. No. 12/387,444 filed May 1, 2009 (allowed), which is a continuation-in-part of U.S. patent application Ser. No. 12/387,429 filed May 1, 2009 (allowed), which is a continuation-in-part of U.S. patent application Ser. No. 12/387,437 filed May 1, 2009 (abandoned), all of which claim priority to U.S. Provisional Patent Application Ser. No. 61/050,162, filed May 2, 2008 (expired), all of which are hereby incorporated by reference in their entirety.

Latin name of genus: *Miscanthus* sp.
Varietal denomination: 'MBS 1002'.

BACKGROUND

The present disclosure relates to a new and distinct cultivar of hybrid *Miscanthus* originated as a cross from *Miscanthus saccharíflorus* (♀, 4n)×*M. sinensis* (♂, 2n) plants and will be referred to hereafter by its cultivar name 'MBS 1002'. This cultivar represents a new cultivar of *Miscanthus* species, a perennial grass which is grown for biomass production, landscape use, ornamental value, and cold tolerance.

'MBS 1002' was selected for its vigorous growth from a selection field which was established from seedlings. The seedling of the cultivar was obtained from seeds of a polycross of *Miscanthus saccharíflorus* (♀, 4n) and *M. sinensis* (♂ 2n) plants. 'MBS 1002' was generated by crossing a single large-stemmed *M. saccharíflorus* genotype from Japan (accession No.: 93M0005064, ploidy: 4×) as a female parent with a population of 15 *M. sinensis* plants as pollen donors (accession Nos.: 93m0146002, 92M0179020, 92M0179017, 93M0147009, 92M0179016, 93m0146012, 93M0144001, 93m0146017, 92m0086, 92m0179015, 93m0146001, 93M0084, 93m0006005, 93M0006003, 93m0007212, and 93M0013004; ploidy: 2×). From this cross, 158 seedlings were obtained and planted in a field. Based on field observations, one tetraploid variety having high biomass was selected and designated as 'MBS 1002'.

'MBS 1002' is different from *Miscanthus* variety 'MBS 7001' disclosed in the co-pending application U.S. Plant patent application No. 12/387,444. 'MBS 7001' is an about 98% to 100% sterile genotype, and is almost 100% self and cross incompatible. 'MBS 7001' rarely produces a seed and is nonviable. In contrast, 'MBS 1002' is 100% fertile, about 98% self incompatible, and 100% cross compatible. 'MBS 1002' does produce viable seed.

'MBS 1002' is similar to 'MBS 7002' disclosed in the co-pending application U.S. Plant patent application Ser. No. 12/387,429, in that it is a fertile, 4× polyploidy derived from the same *M. sacchariflorus* female and 15 *M. sinensis* male plants. 'MBS 1002' and 'MBS 7002' are half-sibs to each other with known female parent. Feedstock yields are similar for both lines (Tables 1-3). They are siblings and recombine very well together in crossing for producing seed.

According to two and three year data and observations, the two cultivars are different from each other for at least the following characters: (1) 'MBS 1002' is different from 'MBS 7002' in that 'MBS 1002' has greater plant vigor during propagation and field transplanting; (2) 'MBS 1002' propagation output is 2 times faster than 'MBS 7002': When MBS 1002 rhizome propagation is utilized for clonal increase its growth rate from dormant rhizome stage to emerging above ground shoot-leaf stage it is 2× faster than MBS 7002. This is reference to vegetative propagation from rhizomes and not seed. Similar response comparison has been observed with tissue culture propagated plants; (3) 'MBS 1002' expresses earlier field spring green up following dormancy; (4) 'MBS 1002' has slightly better cold tolerance than 'MBS 7002'; (5) 'MBS 1002' expresses similar basal circumferences at maturity, but individual culm diameter is significantly greater for 'MBS 1002' over 'MBS 7002' and the check variety 'Illinois clone'. As a result of this last difference, 'MBS 1002' has significantly greater compression circumference than 'MBS 7002' and 'Illinois clone' (Table 4).

TABLE 1

First Year Yield Comparisons 6 locations*

| Entry | % Moist | Yield dt/ac** | Rk |
|---|---|---|---|
| *M.* × *giganteus* 'Illinois clone' | 17.4 | 7.64 | 1 |
| 'MBS 7002'-syn1 | 20.9 | 7.06 | 3 |
| 'MBS 7004'-syn1 | 21.5 | 6.21 | 4 |
| 'MBS 1002'-syn1 | 21.8 | 7.1 | 2 |
| Grand Mean | 19.8 | 7.0025 | |
| LSD(.05) | 3 | 1.42 | |
| CV | | 9.087 | |

*Locations: Auburn, AL, Leland, MS, Starkville, MS, New Castle, KY, Providence Forge, VA, and Champaign, IL
**international unit for dry ton/ acre

TABLE 2

Second Year Yield Comparisons 6 locations*

| Entry | % Moist | Yield dt/ac** | Rk |
|---|---|---|---|
| *M.* × *giganteus* 'Illinois clone' | 28.1 | 8.22 | 4 |
| 'MBS 7002'-syn1 | 28.5 | 9.11 | 2 |
| 'MBS 7004'-syn1 | 26.8 | 9.21 | 1 |
| 'MBS 1002'-syn1 | 29.5 | 8.53 | 3 |
| Grand Mean | 28.4 | 8.7675 | |
| LSD(.05) | 2.9 | 1.02 | |
| CV | | 15.305 | |

*Locations: Auburn, AL, Leland, MS, Starkville, MS, New Castle, KY, Providence Forge, VA, and Champaign, IL
**international unit for dry ton/ acre

TABLE 3

Two-Year Combined Yield Comparisons 6 locations*

| Entry | % Moist | Yield dt/ac** | Rk |
|---|---|---|---|
| *M.* × *giganteus* 'Illinois clone' | 22.8 | 7.93 | 2 |
| 'MBS 7002'-syn1 | 24.7 | 8.09 | 1 |

TABLE 3-continued

Two-Year Combined Yield Comparisons 6 locations*

| Entry | % Moist | Yield dt/ac** | Rk |
|---|---|---|---|
| 'MBS 7004'-syn1 | 24.1 | 7.71 | 4 |
| 'MBS 1002'-syn1 | 25.6 | 7.81 | 3 |
| Grand Mean | 24.3 | 7.89 | |
| LSD(.05) | 2.0 | 0.85 | |
| CV | | 12.976 | |

*Locations: Auburn, AL, Leland, MS, Starkville, MS, New Castle, KY, Providence Forge, VA, and Champaign, IL
**international unit for dry ton/ acre

TABLE 4

First Year Morphological Yield trait comparisons among 'MBS 7002, 'MBS 1002' and *M. giganteus*, cv. Ill Clone. Data represents four locations*, multi-plants measurements per replication on second year mature established plants.

| Entry | Basal Circumference (cm) | Compressed Circumference (cm) | Culm Diameter (mm) | Culm Length (cm) |
|---|---|---|---|---|
| *M.* × *giganteus* 'Illinois clone' | 113.8 A** | 30.1 C | 8.2 B | 273.2 A |
| 'MBS 7002'-syn1 | 88.5 B | 32.6 B | 8.5 B | 254.9 AB |
| 'MBS 1002'-syn1 | 89.2 B | 37.4 A | 10.1 A | 251.7 B |
| Mean | 97.2 | 33.4 | 8.9 | 259.9 |
| LSD 0.05 | 9.4 | 3.7 | 1.4 | 14.3 |
| cv | 3.7 | 7.3 | 10.1 | 3.7 |

*Locations: Auburn, AL, New Castle, KY, Providence Forge, VA, Champaign, IL
**The letters changes represent statistically significant difference between entries based on the LSD range value. It indicates significant separation among entries without having to calculate using the value.

The plant was established asexually from sterile rhizome buds in Klein-Wanzleben, Germany by the inventor. The shoot material was propagated on rooting media and the rooted plantlets were planted into pots in the greenhouse. The plants were planted into the field after one cold period. The characteristics of this cultivar have been determined to be stable and are reproduced true to type in successive generations.

SUMMARY

'MBS 1002' (a.k.a. 'MBS 7005' or 'MBX 006')

The following traits have been repeatedly observed and represent the characteristics of the new cultivar. The new cultivar 'MBS 1002' has not been observed under all possible environmental conditions. The phenotype may vary somewhat with variations in temperature, day-length, light intensity, soil types, and water and fertility levels without, however, any variance in genotype. The color references are made to The Royal Horticultural Society Colour Chart, 1995 Edition.

The following traits have been repeatedly observed and are determined the basic characteristics of 'MBS 1002', which in combination distinguish this *Miscanthus* hybrid from the known *Miscanthus*×*giganteus* and other ornamental *M. sinensis* forms. Plants for the botanical measurements in the present application are two and three-year-old plants. These plants would be considered as mature plants.

1. Vigorous growth
2. Top leaf height about 2.6 meters
3. Green leaves, no colored stripes are present
4. High biomass yield
5. High tiller density 'MBS 1002' (a.k.a. 'MBS 7005' or 'MBX 006') can be distinguished from the *Miscanthus* cultivars 'Strictus' (not patented, a.k.a 'Porcupine grass'), 'Super Stripe' (U.S. Plant Pat. No. 18,161), 'Gold Bar' (U.S. Plant Pat. No. 15,193), 'Little Zebra' (U.S. Plant Pat. No. 13,008) and 'Mysterious Maiden' (U.S. Plant Pat. No. 16,197) in that 'MBS 1002' has no stripes or colored bands on its leaves.

The plant can be propagated by rhizomes, from meristem or nodes. This further distinguishes 'MBS 1002' from *M. sinensis* in that *M. sinensis* cannot be propagated by nodes. 'MBS 1002' aka 'MBS 7005', was selected for its vigorous growth from a selection field which was established from seedlings. It is propagated as a single plant and is used as a parent use for seeded varieties. It can be propagated from Rhizomes and will be utilized as main parent for the described MBS F1/Syn1 cultivars. (See Tables 1-10 for performance and comparisons to other cultivars and the check variety *M. giganteus,* cv. 'Illinois Clone'). The plant was established asexually from rhizome buds at Klein-Wanzleben, Germany by the inventor company. The shoot material was propagated on rooting media and the rooted plantlets were planted into pots in the greenhouse. The plants were planted into the field after one cold period. The characteristics of this cultivar have been determined to be stable and are reproduced true to type in successive generations.

BRIEF DESCRIPTION OF THE DRAWINGS

The accompanying color photograph in FIG. 1 illustrates the detailed appearance and distinct characteristics of the new *Miscanthus* cultivar 'MBS 1002'.

FIG. 1D shows 'MBS 1002' plants at mid flower stage (MFS); FIG. 1E shows 'MBS 1002' plants 20 days post mid flower stage.

FIG. 1F shows an inflorescence of 'MBS 1002' at mid flower stage; FIG. 1G shows an inflorescence of 'MBS 1002' 10 days post mid flower stage; FIG. 1H shows an inflorescence of 'MBS 1002' 20 days post mid flower stage and an inflorescence 34 days post mid flower stage; FIG. 1I shows an inflorescence of 'MBS 1002' 38 days post mid flower stage and an inflorescence 42 days post mid flower stage; FIG. 1J shows an inflorescence of 'MBS 1002' 49 days post mid flower stage; FIG. 1K shows an inflorescence of 'MBS 1002' 52 days post mid flower stage.

DETAILED BOTANICAL DESCRIPTION OF THE PLANTS

Figure 1A:
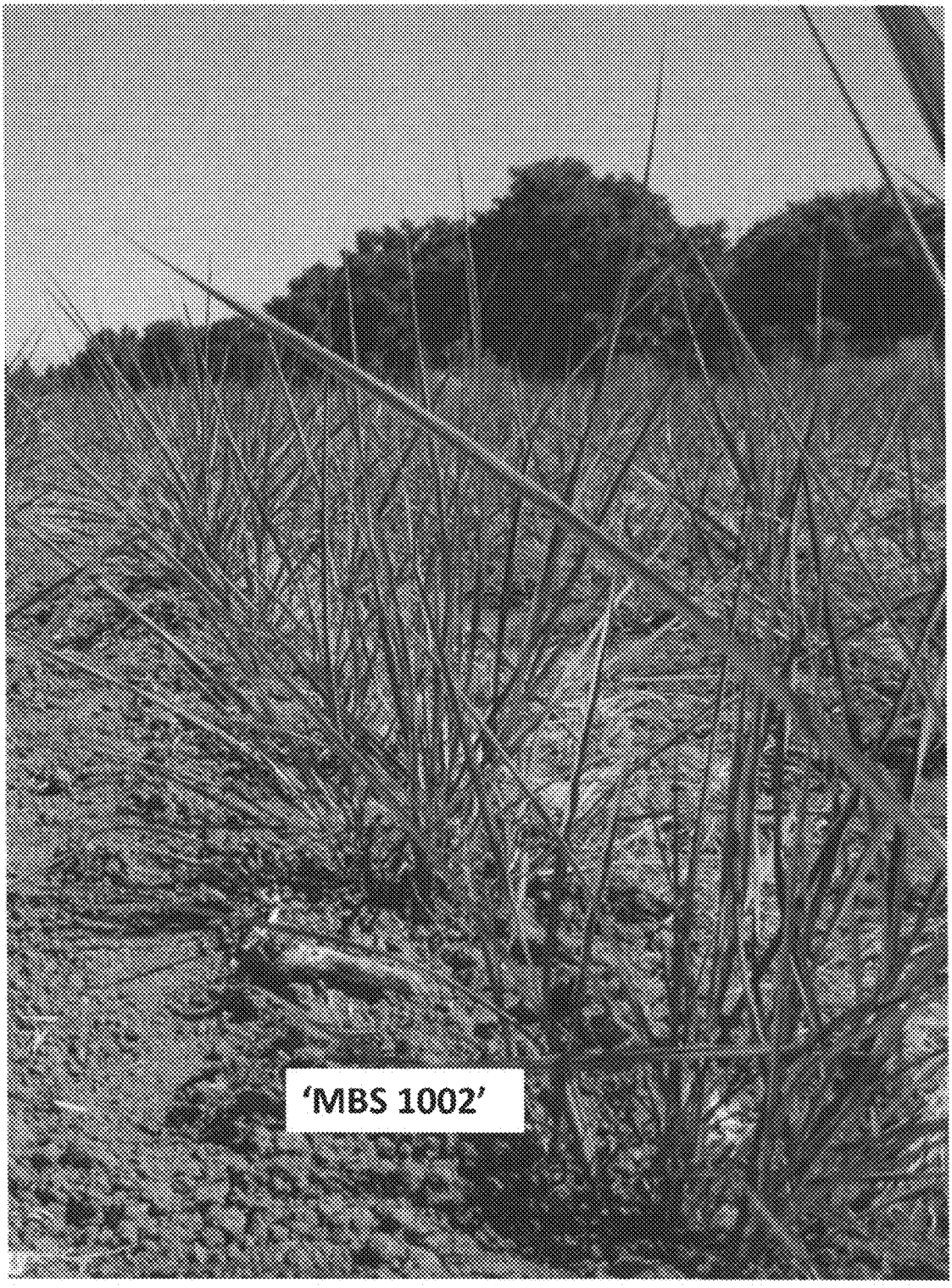
FIG. 1A and FIG. 1B show young 'MBS 1002' plants.
Figure 1B:
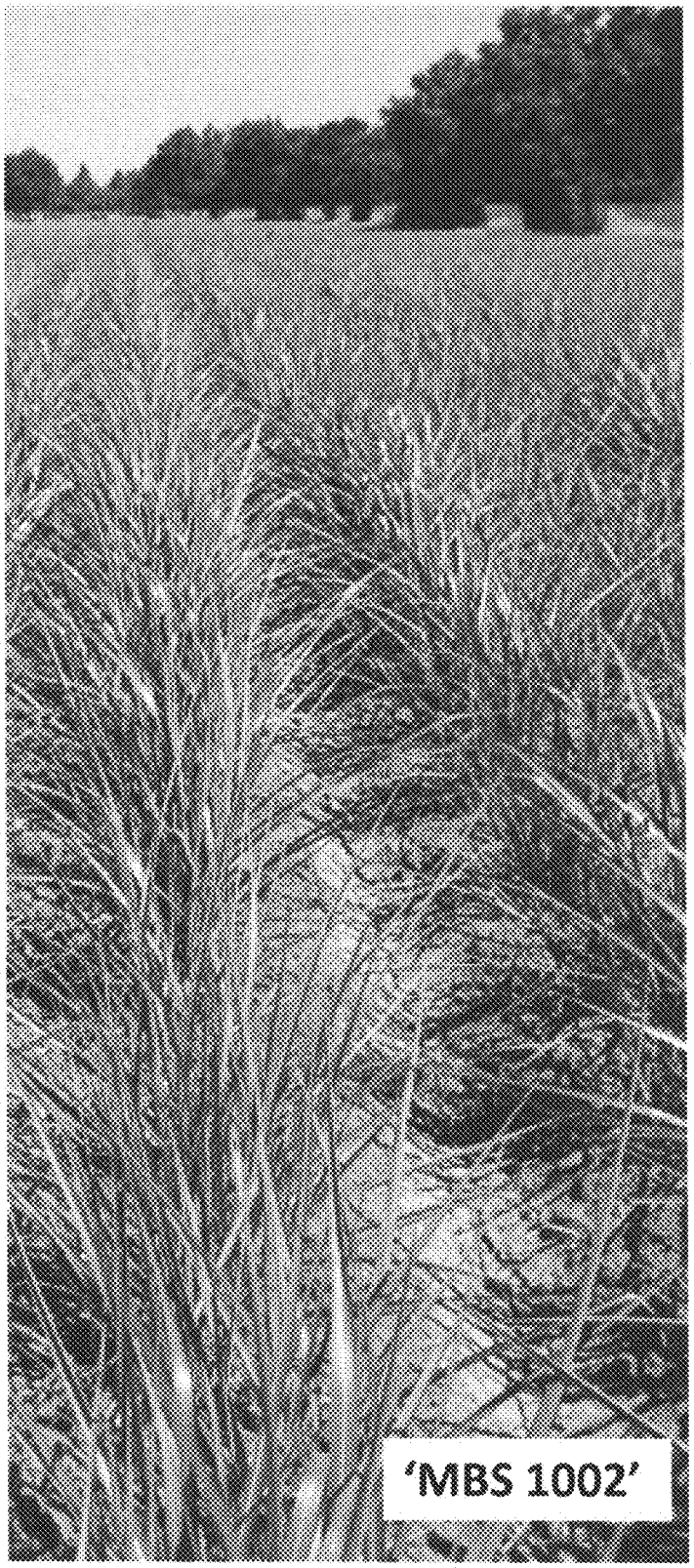
Figure 1C:
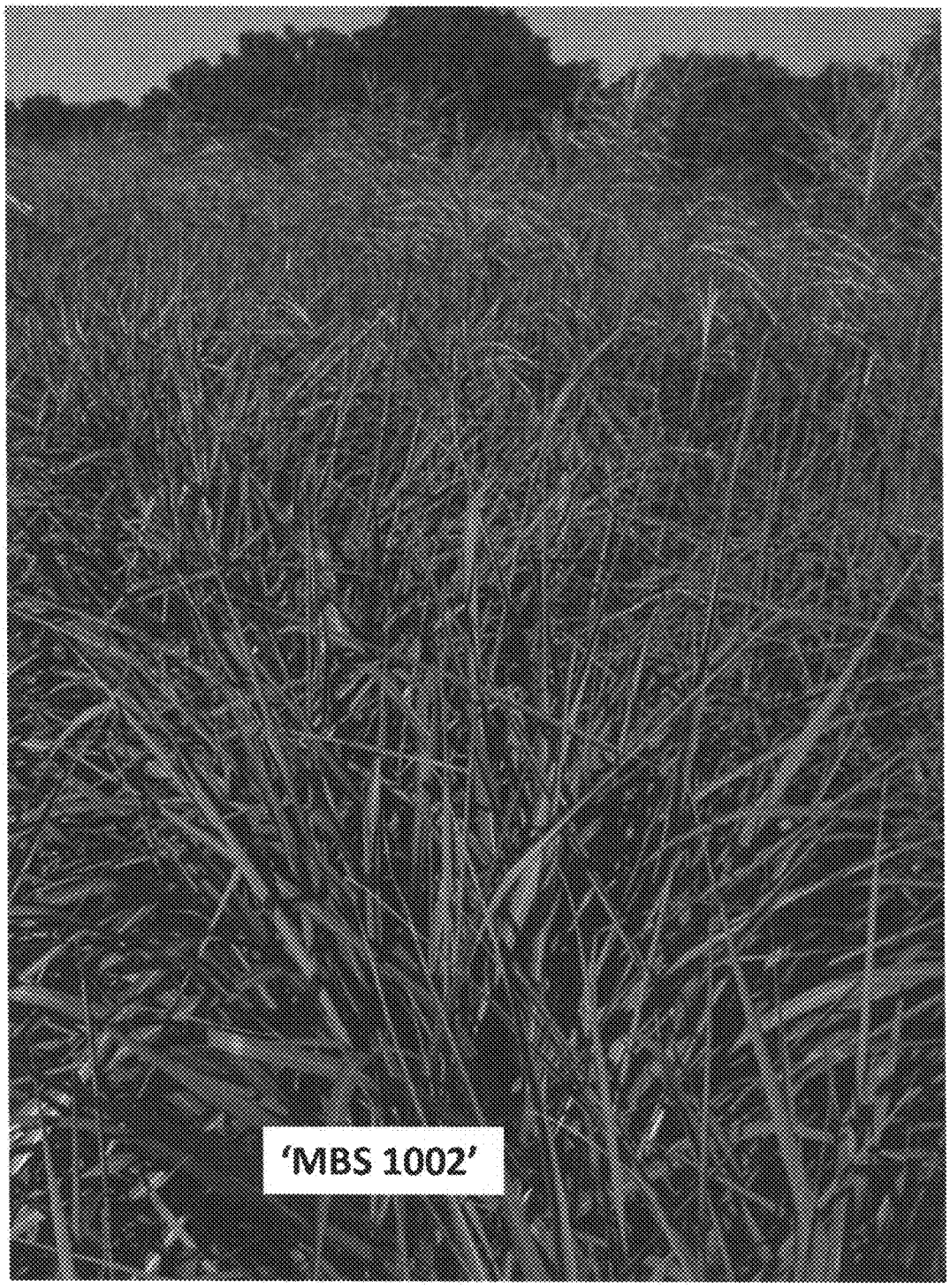
FIG. 1C to FIG. 1E show flowing 'MBS 1002' plants. Specifically.
Figure 1D:
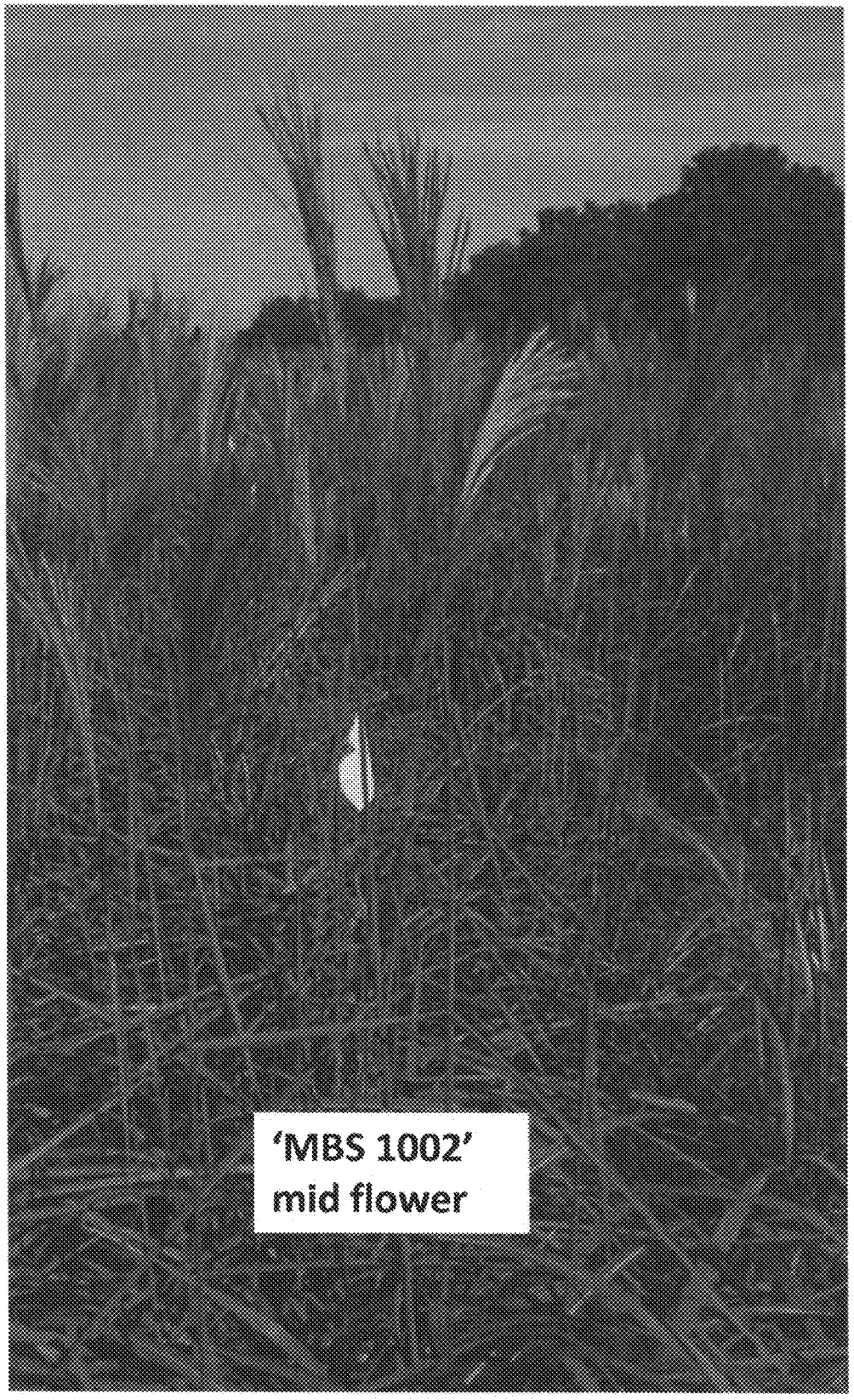
Figure 1E:
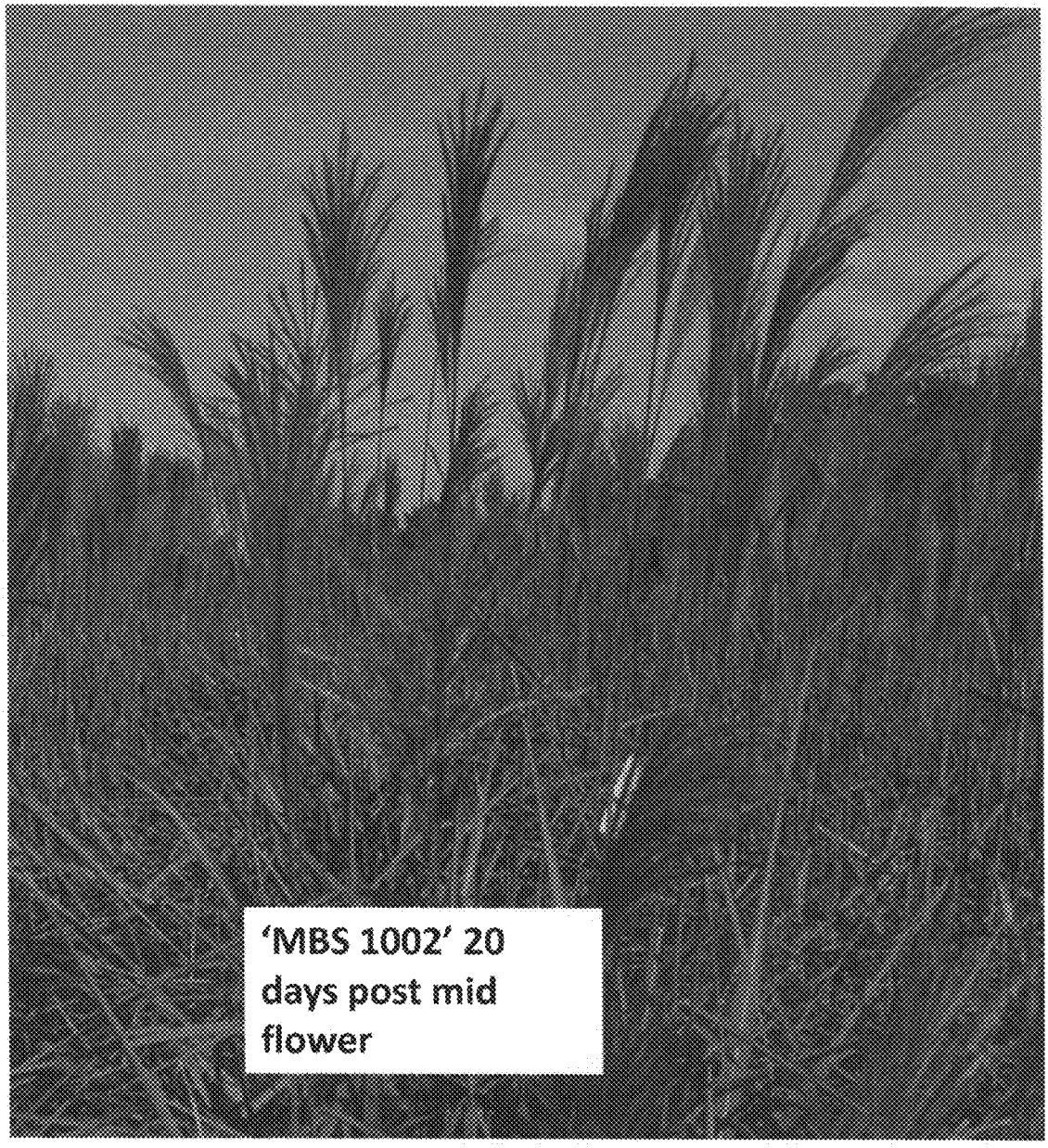
Figure 1F:
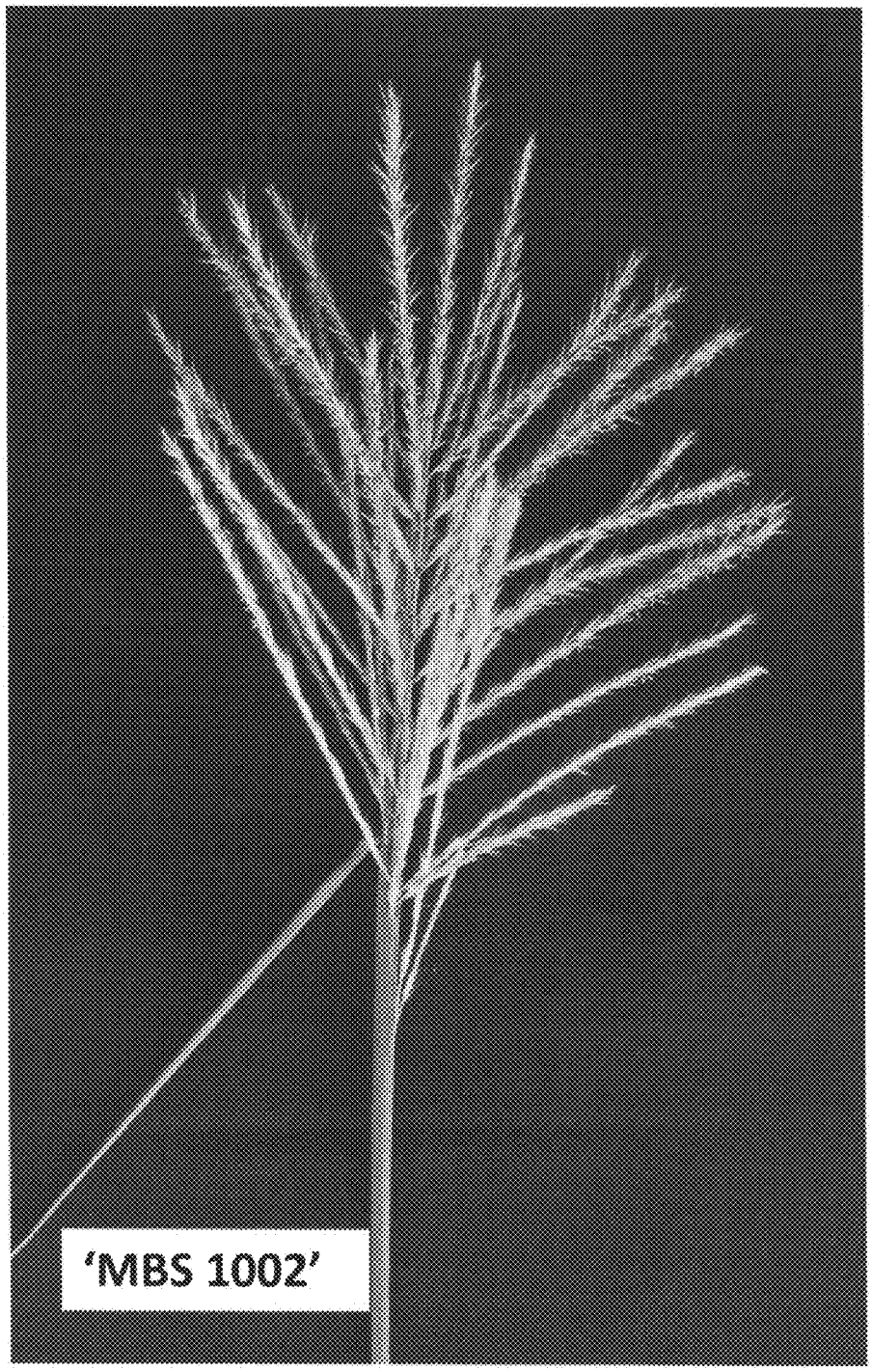
FIG. 1F to FIG. 1K show inflorescences of 'MBS 1002'. Specifically.
Figure 1G:
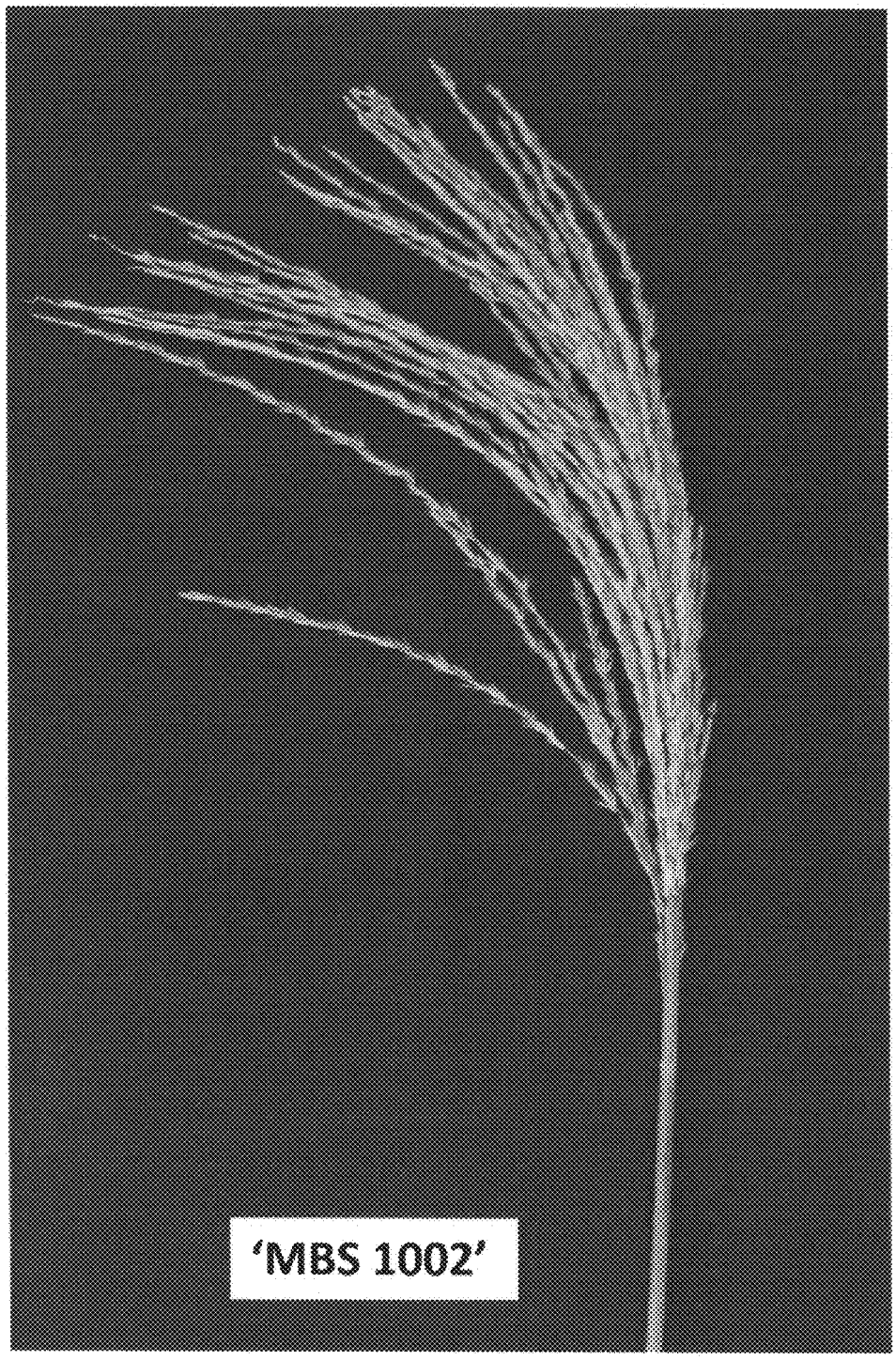
Figure 1H:
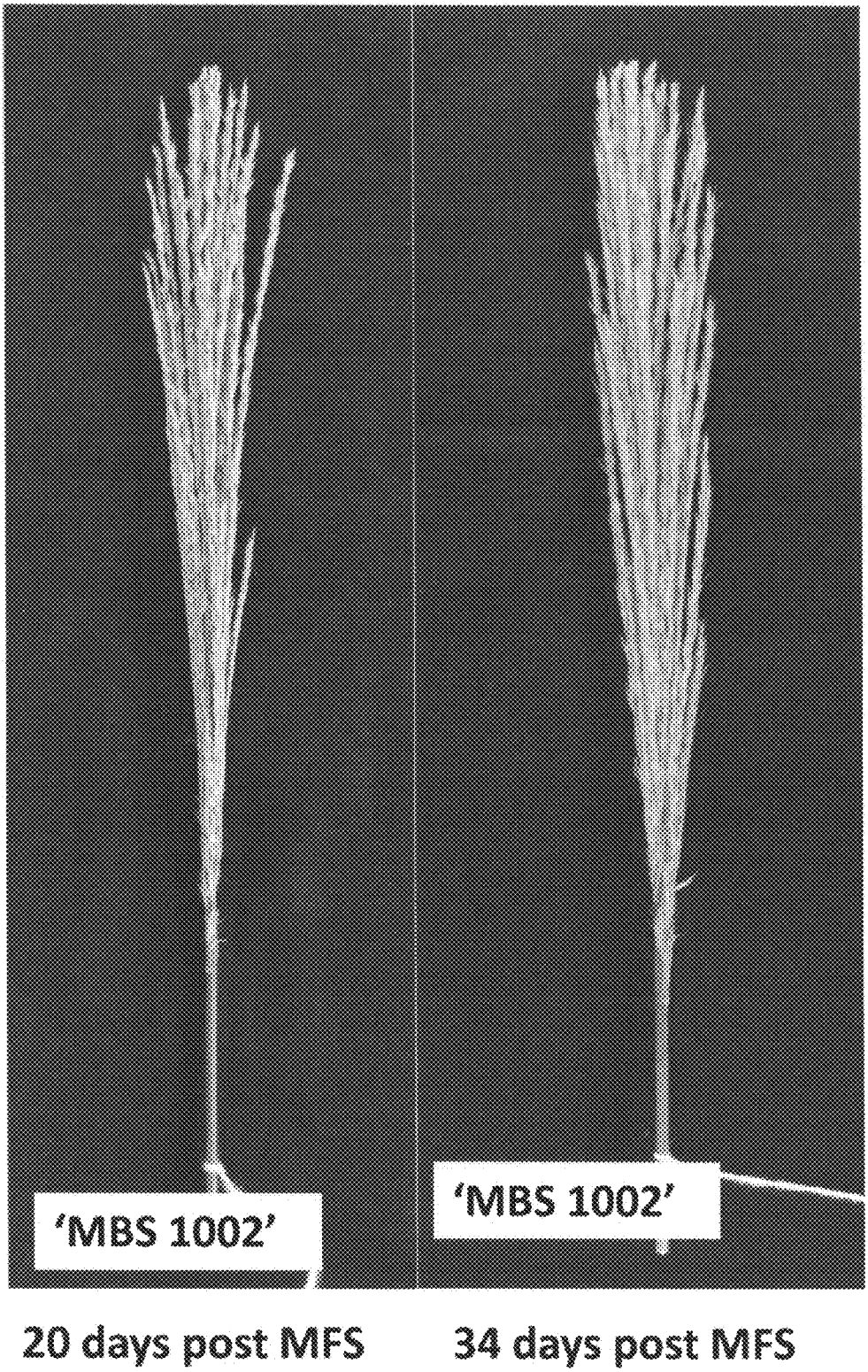
Figure 1I:
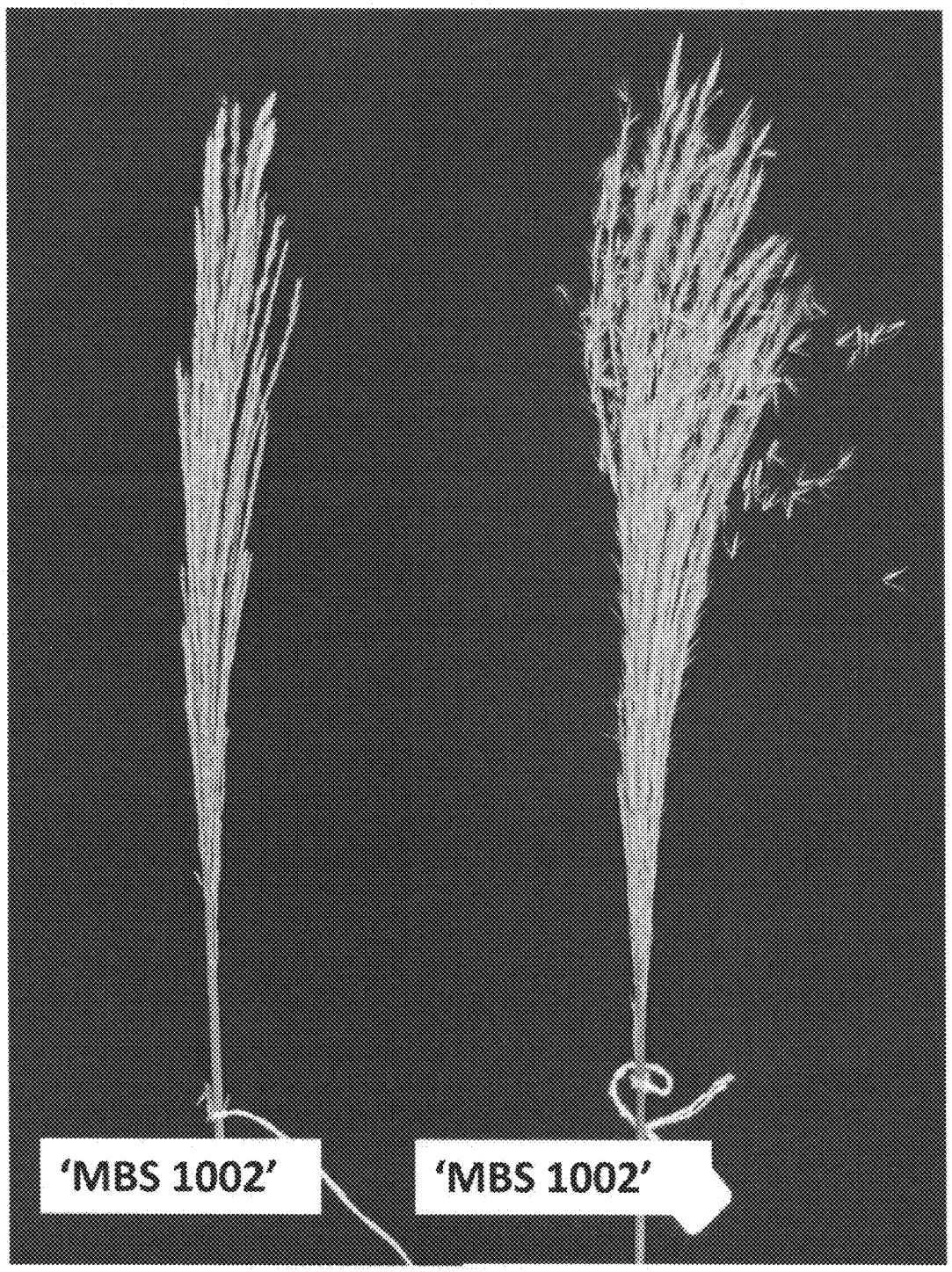
Figure 1J:
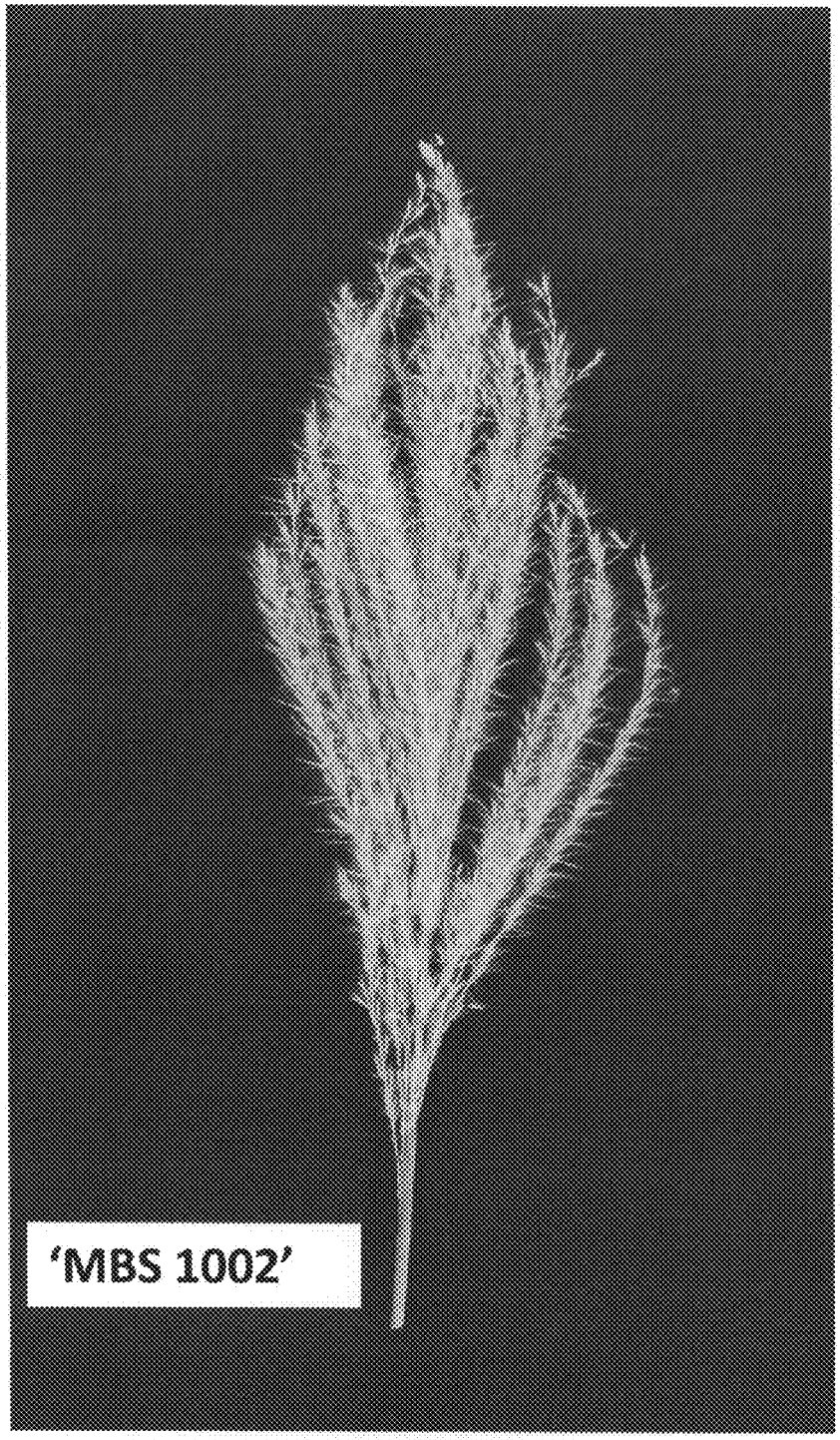
Figure 1K:
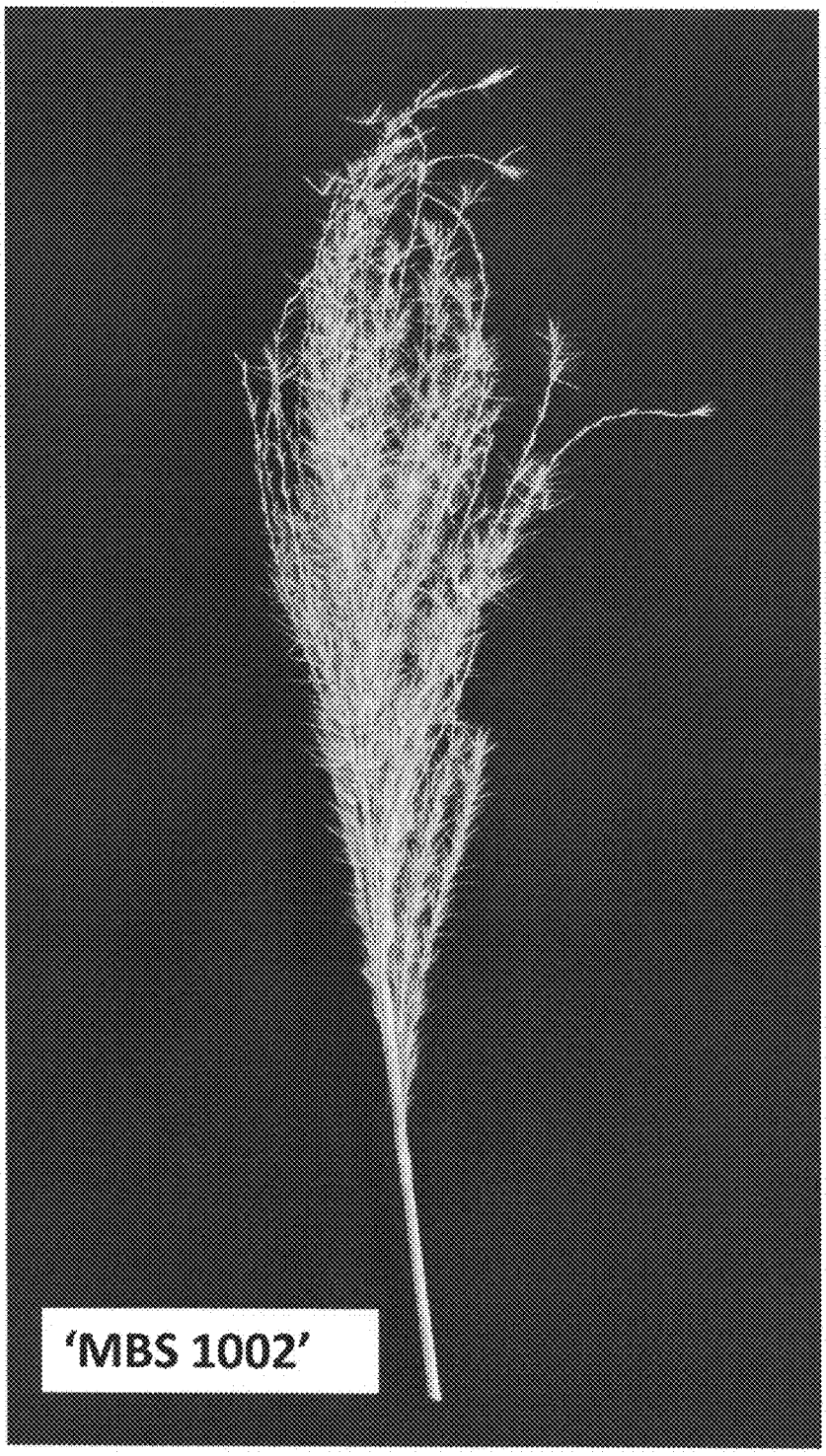

'MBS 1002' has not been observed under all possible environmental conditions, and the phenotype may vary significantly with variations in environment. The following observations, measurements, and comparison describe this plant as grown at Klein-Wanzleben, Germany, when grown in the field. All observations were recorded during the plant's dormant season (April 2008) and the 2007 and 2008 growing season unless otherwise noted.

Botanical classification: 'MBS 1002' is a fertile hybrid of a cross from *Miscanthus sinensis* and *Miscanthus sacchariflorus*.

Common name: Maiden grass

Parentage: Polycross of *M. sacchariflorus* and several *M. sinensis*

General description:

*Blooming period.*—'MBS 1002' blooms in late fall in the southern and central US. Blooms at the end of September in Klein-Wanzleben (north central), Germany. Blooms are retained over the winter.

*Plant habit.*—Herbaceous, tuft forming, with upright culms.

*Height and spread.*—Top leaf height about 2.6 meters.

*Hardiness.*—Productive growth in Klein-Wanzleben (north central), Germany.

*Culture.*—Best in sandy loam, well-drained soil, higher yields in warmer climates and higher soil fertility.

*Diseases and pests.*—In the United States, 'MBS 1002' has shown excellent resistance to lesser stem borer spp. when compared to the public check variety *M. giganteus* cv. 'Illinois clone'. Observations and confirmation on stem borer tolerance occurred during early growth stages within 2-8 weeks after field planting of seedling material. These findings have been observed in southern Georgia and Central Indiana. Predominantly, resistance expression has been observed across locations in southeastern US.

The Tables 5 to 8 (below) provide data for average basal circumference, average compression circumference, average culm diameter, and average culm length of 'MBS 1002', as compared to *M.×giganteus* cv. 'Illinois clone':

TABLE 5

Average Basal Circumference in cm*.

| Entry | Auburn, AL | Champaign, IL | Jerseyville, IL | Leland, MS | Starkville, MS | Entry Means |
|---|---|---|---|---|---|---|
| MBS 1002 '7005' syn l | 101 | 81 | 78 | 98 | 88 | 89 |
| *M.* × *giganteus* 'Illinois' | 91 | 131 | 107 | 71 | 113 | 103 |
| Location Means | 96 | 98 | 87 | 91 | 93 | 93 |

*Data from 2 year old mature plants.

TABLE 6

Average Compression Circumference in cm*.

| Entry | Auburn, AL | Champaign, IL | Jersey-ville, IL | Leland, MS | New Castle, KY | Providence Forge, VA | Stark-ville, MS | Entry Mean |
|---|---|---|---|---|---|---|---|---|
| 'MBS 1002' '7005' syn l | 48 | 31 | 36 | 17 | 37 | 34 | 30 | 34 |
| *M.* × *giganteus* 'Illinois' | 23 | 28 | 35 | 11 | 36 | 31 | 25 | 27 |
| Location Means | 35 | 29 | 35 | 15 | 37 | 33 | 27 | 30 |

*Data from 2 year old mature plants

TABLE 7

Average of Culm Diameter in cm*.

| Entry | Auburn, AL | Champaign, IL | Jersey-ville, IL | Leland, MS | New Castle, KY | Providence Forge, VA | Stark-ville, MS | Entry Mean |
|---|---|---|---|---|---|---|---|---|
| 'MBS 1002' '7005' syn l | 6.1 | 9.4 | 6.9 | 6.8 | 7.0 | 6.7 | 6.0 | 7.0 |

TABLE 7-continued

| Average of Culm Diameter in cm*. | | | | | | | | |
|---|---|---|---|---|---|---|---|---|
| Entry | Auburn, AL | Champaign, IL | Jerseyville, IL | Leland, MS | New Castle, KY | Providence Forge, VA | Starkville, MS | Entry Mean |
| *M.* × *giganteus* | 5.7 | 8.4 | 8.2 | 5.9 | 7.3 | 6.5 | 5.0 | 6.7 |
| 'Illinois' | | | | | | | | |
| Location Means | 6.1 | 8.8 | 7.5 | 6.2 | 7.2 | 6.6 | 5.2 | 6.8 |

*Data from 2 year old mature plants

TABLE 8

| Average of Culm Length (cm) | | | | | | | | |
|---|---|---|---|---|---|---|---|---|
| Entry | Auburn, AL | Champaign, IL | Jerseyville, IL | Leland, MS | New Castle, KY | Providence Forge, VA | Starkville, MS | Entry Mean |
| 'MBS 1002' | 242 | 263 | 224 | 204 | 234 | 246 | 182 | 228 |
| '7005' syn 1 | | | | | | | | |
| *M.* × *giganteus* | 193 | 291 | 283 | 172 | 270 | 283 | 214 | 244 |
| 'Illinois' | | | | | | | | |
| Location Means | 225 | 270 | 252 | 203 | 255 | 265 | 199 | 238 |

*Data from 2 year old mature plants

Growth and propagation:

*Propagation.*—By culm division, in vitro culture, from rhizomes, meristem or axillary buds (nodes).

*Growth rate.*—Vigorous.

The following descriptions are based on data from 2-3 year old plants, which are considered mature plants.

Culm (stem) description:

*General description.*—Cylindrical, pithy, reed-like, erect, sheathed. 15-17 leaves per culm.

*Culm aspect.*—Rigid and held erect, none are cascading.

*Culm color* (*dormant season*).—Yellowish, lower internodes partly reddish brown/orange (RHS 167B-167C). Midsummer color is green to dark green (RHS 144A-146B) in Germany and the US; end of season is brown. End of season culm color in the US-Lafayette, Ind. to Southern GA range is RHS 164B at culm base to 162D at culm top past final node; lower internodes predominantly red-pink to violet (RHS N77B) with some green (RHS 144A-146C), and vary with intensity depending on location and growing conditions. The rate at which the culm color changes is dependent on location, with the change from green to dormancy brown as described herein being more rapid in the northern latitudes when the days become increasingly shorter.

*Culm size.*—Average about 0.73 cm in diameter, and up to about 2.6 m in height on mature plants.

*Culm circumference.*—2.8 cm.

*Plant basal circumference.*—193 cm.

*Plant compressed circumference.*—38.1 cm.

*Culm surface.*—Culm is covered with a few hairs on the leaf sheaths.

*Internode length.*—6 to 18 cm.

*Ligule.*—Membranous, about 3 mm (*M.×giganteus* is 2.5-3 mm), reddish color 59D, longest hair is 1.5 mm (gig 1 mm), encircles the entire culm, inner surface is glabrous, hairs on the outer surface, on entire ligule, hairs are approximately 4 mm (*M.×giganteus:* 4-5 mm).

Foliage description:

*General.*—No hairs on upper and lower leaf surface, some larger hairs on upper surface near ligula.

*Leaf shape.*—Linear.

*Leaf base.*—Sheathed.

*Leaf division.*—Simple.

*Leaf apex.*—Acuminate.

*Leaf aspect.*—Emerging leaves are erect, blades are convex, leaf angle younger leaves 50°, leaf angle older leaves 10°.

*Leaf tip younger leaves.*—½ pendently, meaning approximately half of the leaf tip area of the younger leaves bend downward.

*Leaf venation.*—Parallel, leaf venation upper surface concave, lower surface convex, mid-rib color is whitish.

*Leaf margins.*—Entire, visible, sharp short bristles under the microscope.

*Leaf size.*—Up to 90 cm, width: 2-2.8 cm.

*Leaf persistence.*—Foliage dries and is generally retained on the stem during winter.

*Leaf attachment.*—Sheathed.

*Leaf arrangement.*—Alternate, tapering.

*Leaf surface.*—Upper-light glossy, lower-matte.

*Leaf color* (*during growing season*).—Green, no stripes, 146A.

Flower description:

*General description.*—Compact, fan-shaped panicle terminating from each culm in mid to late September.

*Angle of raceme.*—45°.

*Persistence of inflorescence.*—Panicles are persistent from fall through winter.

*Fragrance.*—None.

*Panicle size.*—Average of 36 cm in length, not completely emerged at time of measurement, 17 cm in width at one field trial location.

*Panicle color.*—Varies 153C-174B The intensity of these color grades depends on location and growing conditions, and varies during plant development. This color report indicates that 174B would be early panicle appearance and 153C is for mature panicle appearance.

*Spikelet description.*—Spikelets in pairs, awn: 2 mm.

*Spikelet size.*—About 4 mm in length and 1 mm in width (excluding hairs).

*Spikelet hairs.*—Average of 12 mm in length, 186B in color.

*Spikelet color.*—181A.

Reproductive organ description:

*Androecium.*—Anthers; 3 mm in length and 0.5 mm in width, 187A or 4C in color, reddish or yellow.

*Gynoecium.*—Stigma color is 187A, red, 3 mm in length and 0.5 mm in width.

*Caryopsis.*—Produces fertile seeds.

'MBS 1002' produces a small elliptical seed, about 2-2.5 mm in length. Healthy seed is clear amber to dark brown RHS 167B-200A. It is a heavy anemochore (wind dispersal) with an average seed weight of 0.96 mg, a chamaephyte (buds permanently above ground) life form, with an annual seed production of 64-1200 seeds per plant depending upon pollen source availability.

Yield: The average yield of 'MBS 1002' compared to *M.×giganteus* cv. 'Illinois' is shown below in Table 9.

TABLE 9

Average Yield (tons/ac) in U.S.*

| Material name | Auburn, AL | Champaign, IL | Providence Forge, VA | Leland, MS | New Castle, KY | Jerseyville, IL | Starkville, MS | Mean |
|---|---|---|---|---|---|---|---|---|
| 'MBS 1002' '7005' syn 1 | 5.07 | 11.1 | 5.3 | 9.8 | 10.6 | 5.3 | 3.8 | 7.3 |
| *M.* × *giganteus* 'Illinois' | 2.56 | 13.6 | 5.3 | 4.7 | 11.6 | 6.1 | 5.0 | 7.0 |
| Location Means | 3.98 | 12.1 | 5.4 | 8.3 | 10.8 | 5.1 | 4.5 | 7.2 |
| LSD .05 | 2.6 | 3.1 | 1.3 | 3.8 | 2.4 | 3.2 | 1.8 | 1.5 |

*Data from 2 year old mature plants

Moisture: The average moisture of 'MBS 1002' compared to *M.×giganteus* cv. 'Illinois' is shown below in Table 10.

TABLE 10

Average % Moisture content at harvest in U.S*.

| Material name | Auburn, AL | Champaign, IL | Providence Forge, VA | Leland, MS | New Castle, KY | Jerseyville, IL | Starkville, MS | Entry Mean |
|---|---|---|---|---|---|---|---|---|
| 'MBS 1002' '7005' syn 1 | 18 | 32 | 24 | 22 | 34 | 32 | 7 | 24 |
| *M.* × *giganteus* 'Illinois' | 19 | 26 | 21 | 13 | 30 | 11 | 12 | 19 |
| Location Means | 19 | 30 | 22 | 17 | 31 | 21 | 9 | 21 |
| LSD 0.05 | 1.1 | 2.3 | 2.4 | 3.4 | 2.1 | 4.1 | 2.7 | 3.3 |

*Data from 2 year old mature plants

*M.×giganteus* is also a cross between *M. saccharaflorus* (4×) and *M. sinensis* (2×) resulting in a sterile clone plant selection that is available to the public. This is how 'MBS 1002' was derived, only using different parentage in the ploy-cross as described. Therefore *M.×giganteus* (3×) cv 'Illinois clone' is an excellent cultivar for comparison with novelty claims.

The invention claimed is:

1. A new and distinct cultivar of *Miscanthus* plant named 'MBS 1002', substantially as herein shown and described.

* * * * *

Mid Flower Stage 10 days post Mid Flower Stage 38 days post MFS 42 days post MFS 49 days post MFS 52 days post MFS